(12) United States Patent
Bruckner et al.

(10) Patent No.: US 11,351,295 B2
(45) Date of Patent: Jun. 7, 2022

(54) DRAINAGE TUBE AND TREATMENT KIT WITH DRAINAGE TUBE

(71) Applicant: LOHMANN & RAUSCHER GMBH, Schonau/Triesting (AT)

(72) Inventors: Gunter Bruckner, St. Lorenz (AT); Sonja Grillitsch, Vienna (AT)

(73) Assignee: LOHMANN & RAUSCHER GmbH, Schoenau an der Triesting (AT)

( * ) Notice: Subject to any disclaimer, the term of this patent is extended or adjusted under 35 U.S.C. 154(b) by 394 days.

(21) Appl. No.: 16/463,536

(22) PCT Filed: Sep. 5, 2017

(86) PCT No.: PCT/EP2017/072203
§ 371 (c)(1),
(2) Date: May 23, 2019

(87) PCT Pub. No.: WO2018/095603
PCT Pub. Date: May 31, 2018

(65) Prior Publication Data
US 2020/0078500 A1      Mar. 12, 2020

(30) Foreign Application Priority Data
Nov. 28, 2016   (DE) .......................... 102016014190.5

(51) Int. Cl.
*A61M 1/00*   (2006.01)
*A61M 25/00*  (2006.01)
(Continued)

(52) U.S. Cl.
CPC .......... *A61M 1/964* (2021.05); *A61M 25/007* (2013.01); *A61M 25/0026* (2013.01);
(Continued)

(58) Field of Classification Search
CPC .............. A61M 1/964; A61M 25/0026; A61M 25/007; A61M 25/0071; A61M 25/0108;
(Continued)

(56) References Cited

U.S. PATENT DOCUMENTS 4,717,379 A * 1/1988 Ekholmer ........... A61M 25/007
604/43
4,968,307 A * 11/1990 Dake ................... A61M 25/007
604/264

(Continued)

OTHER PUBLICATIONS

MED-6015 | Optically Clear Low Viscosity Silicone Elastomer | Avantor. https://www.avantorsciences.com/nusil/en/product/MED-6015/optically-clear-low-consistency-silicone-elastomer. Accessed Mon Sep. 13, 2021.*

(Continued)

*Primary Examiner* — Adam Marcetich
(74) *Attorney, Agent, or Firm* — Stinson LLP

(57) ABSTRACT

Drainage tube for use in wound drainage, in particular in deep drainage, having a drainage lumen surrounded by a tube jacket and extending parallel to the tube axis, the tube jacket having at least one perforation which, starting at an outer boundary area of tube jacket, extends in a transverse direction, in particular approximately perpendicular to the tube axis, and opens out into the drainage lumen.

24 Claims, 3 Drawing Sheets

Figure 1:
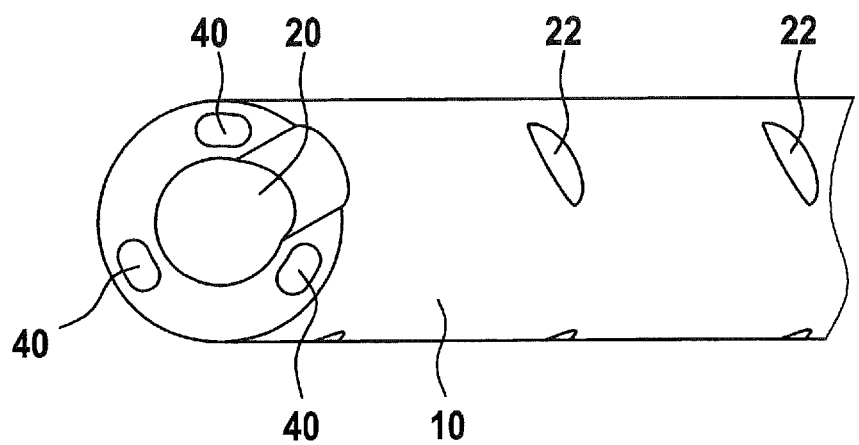

(51) Int. Cl.
*A61M 25/01* (2006.01)
*A61M 27/00* (2006.01)

(52) U.S. Cl.
CPC .... *A61M 25/0071* (2013.01); *A61M 25/0108* (2013.01); *A61M 27/002* (2013.01); *A61M 2025/004* (2013.01); *A61M 2027/004* (2013.01)

(58) Field of Classification Search
CPC .......... A61M 27/002; A61M 2025/004; A61M 2027/004; A61M 27/00
See application file for complete search history.

(56) References Cited

U.S. PATENT DOCUMENTS

| | | | | |
|---|---|---|---|---|
| 5,004,455 | A * | 4/1991 | Greenwood | A61M 25/0017 604/264 |
| 5,360,414 | A * | 11/1994 | Yarger | A61M 25/0043 604/264 |
| 5,370,610 | A * | 12/1994 | Reynolds | A61M 25/003 604/43 |
| 5,425,723 | A * | 6/1995 | Wang | A61M 25/007 138/114 |
| 5,599,307 | A * | 2/1997 | Bacher | A61F 2/82 604/101.05 |
| 2002/0049402 | A1 * | 4/2002 | Peacock, III | A61B 17/12045 604/8 |
| 2004/0147864 | A1 * | 7/2004 | Lenker | A61M 1/3656 604/4.01 |
| 2007/0219471 | A1 | 9/2007 | Johnson et al. | |
| 2008/0172013 | A1 * | 7/2008 | Kucklick | A61M 5/14 604/288.03 |
| 2010/0168714 | A1 * | 7/2010 | Burke | A61M 25/1002 604/509 |
| 2011/0213319 | A1 | 9/2011 | Blott et al. | |
| 2012/0165791 | A1 * | 6/2012 | Lovmar | A61M 25/0017 604/544 |
| 2012/0226103 | A1 * | 9/2012 | Gunday | A61M 25/0155 600/118 |
| 2013/0073015 | A1 * | 3/2013 | Rozenberg | A61K 9/007 607/106 |
| 2014/0330224 | A1 * | 11/2014 | Albert | A61M 1/90 604/319 |
| 2015/0290367 | A1 | 10/2015 | Hertwig et al. | |
| 2016/0271363 | A1 * | 9/2016 | Bauer | A61M 25/0026 |
| 2016/0287278 | A1 * | 10/2016 | Stigall | A61B 17/2202 |
| 2017/0049997 | A1 * | 2/2017 | Chao | A61M 25/0075 |
| 2017/0232238 | A1 * | 8/2017 | Biller | A61M 25/1011 604/509 |

OTHER PUBLICATIONS

International Search Report and Written Opinion dated Oct. 20, 2017 for related PCT/EP2017/072203 filed Sep. 5, 2017.

* cited by examiner

DRAINAGE TUBE AND TREATMENT KIT WITH DRAINAGE TUBE

The invention relates to a drainage tube for use in wound drainage, in particular in deep drainage, having a drainage lumen surrounded by a tube jacket and extending parallel to the tube axis, as well as a treatment kit equipped with such a drainage tube.

Drainage tubes are required in wound care for draining wound fluid, in particular exudates, i.e. inflammation-related discharges from the wound.

In some cases, in order to promote wound drainage and the overall wound healing process, a negative pressure is also generated in the area of the wound. For this purpose, the drainage lumen of a drainage tube may be connected to a device for generating a negative pressure, such as a pump, on the side facing away from the wound. In this case, the wound space is usually closed off by way of an occlusive film, in order to counteract any pressure compensation in the wound space. At the same time, to promote drainage, aeration of the wound space may also be provided in the drainage lumen in order to maintain a flow draining off the wound fluid. In particular in the treatment of deep-seated wounds, hence in deep drainage, it has been shown that only insufficient drainage of the wound fluid from the wound space is achieved, even if a negative pressure and possibly also flow-promoting aeration are used.

In view of these problems in the state-of-the-art, the invention is based on the object of providing a drainage tube by means of which wound drainage can be assured even in the case of deep-seated wounds.

According to the invention, this object is achieved by an enhancement of the prior art drainage tubes, which is essentially characterized in that the tube jacket has at least one perforation, which, starting at an outer boundary area of the tube jacket, extends in a transverse direction, in particular approximately perpendicular to the tube axis and opens out into the drainage lumen.

Using drainage tubes enhanced according to the invention, the aspiration of wound fluid, in particular of exudates, can take place over a larger area, i.e. the frontal opening area of the drainage lumen and the opening area of the perforation in the area of the outer boundary area of the drainage tube. This assures that even in the case of deep-seated wounds, in which large-area aspiration is required, satisfactory drainage of the wound fluid takes place.

Within the scope of the invention, the improvement of wound drainage in the case of deep-seated wounds can even be achieved using only one perforation of the tube jacket. It has, however, proven to be particularly advantageous if the tube jacket has at least one drainage section of a given length, for example approx. 300 mm, with two, three or a plurality of perforations opening out into the drainage lumen and a line section without any perforation, wherein the axial length of said line section without any perforation is longer than the axial distance between said perforations in said drainage section.

Homogeneous drainage of wound fluids can take place if the perforations are arranged at invariable axial distances from each other. For this purpose, 15 to 25 perforations having axial distances of 5 mm to 20 mm may be provided. This results in a total length of the perforation section of 75 mm to 500 mm. In general, it suffices if the perforation section has a length of 250 mm to 350 mm, in particular approx. 300 mm. The line section may have a length of 400 mm to 700 mm, in particular 500 mm to 650 mm, particularly preferred approx. 600 mm.

For the purpose of aerating the wound space, the tube jacket may also, in addition to the drainage lumen, be penetrated by at least one aeration lumen, which is arranged radially offset thereto and preferably also extends approximately parallel to the tube axis and which is, at least in sections, separated from the drainage lumen by a tube jacket area situated radially inside and has a radial thickness of preferably 0.2 mm to 0.7 mm, in particular at least 0.4 mm. As a result of this arrangement, drainage and aeration of the wound can take place using only one multilumen tube.

In order to assure reliable aeration of the wound, within the scope of the invention, it has proven to be particularly expedient if the tubular jacket is penetrated by two, three or a plurality of aeration lumens, which penetrate the tube jacket and are offset against each other in the circumferential direction of the tube jacket. In this and other embodiments of the invention, the drainage lumen may extend coaxial to the tube axis, while the axes of the aeration lumens are arranged in a radial intersecting plane on a circular line encircling the tube axis. In this case, the aeration lumens are radially offset at equal intervals with respect to the exudate lumen.

The creation of the perforation connecting the tube jacket to the drainage lumen for providing large-area aspiration will be facilitated if the offset between two adjacent aeration lumens in the circumferential direction is larger than 360°/n, where n denotes the number of aeration lumens. The perforation for creating an additional drainage port then takes place in the area between the aeration lumens, which are particularly strongly offset against each other, in order to reduce thereby the risk of any accidental damage to an aeration lumen. Related thereto, it has proven to be particularly expedient if the offset between two adjacent aeration lumens in the circumferential direction of the drainage tube is in the range between 120° and 240°, preferably between 150° and 210°, in particular between 170° and 190°.

Within the scope of the invention, it is particularly preferred if the drainage tube has three aeration lumens. For this purpose, a particularly large distance between two aeration lumens can be created subject to geometrically easily producible conditions if the longitudinal axes of two aeration lumens are situated on a common radial line of the tube and the axis of the drainage lumen. Between two aeration lumens, a tube jacket area is then provided, which extends over a circumferential angle of 180° and is available for creating a perforation, while, on the other hand, an additional aeration lumen can be made available in the remaining circumferential section. If, in the last-described embodiment of the invention, the longitudinal axis of the aeration lumens in a radial intersecting plane form the vertices of a right triangle, while, at the same time, making sure that the longitudinal axis of the aeration lumens are situated on a circular line encircling the tube axis, continuous perforation of the tube having a particularly large perforation radius can take place without any damage to the aeration lumens.

In this respect, it has proven to be particularly expedient if at least one, preferably all, aeration lumens in a radial intersecting plane have a smaller sectional area than the drainage lumen.

It is equivalent to the arrangement of the axes of the aeration lumens on a circular line encircling the tube axis if the aeration lumens have approximately the same radial distances from the longitudinal axis of the drainage lumen, provided the drainage lumen per se is coaxial with the tube axis.

A further improvement of the drainage of wound fluid, in particular of exudates, can be achieved if the aeration of the wound does not take place at only one face of the drainage tube, but if the tube jacket has at least one aeration perforation, which, starting at an outer boundary area of the tube jacket, extends in a transverse direction, in particular approximately perpendicular to the tube axis and opens out into at least one aeration lumen. Aeration of the wound space across this aeration perforation can, additionally or alternatively, take place via frontal openings of the aeration lumens. As the case may be, these frontal openings must be closed or caused to be closed.

The aeration lumens may also be arranged distributed over a given axial length of the drainage tube. For this purpose, the tube jacket has at least one aeration section of a given length having two, three or a plurality of aeration perforations that open out into at least one aeration lumen as well as a line section without any perforation, wherein the axial length of said line section without any perforation is longer than the axial distance between said perforations in said drainage section.

Within the scope of the invention, aeration section and drainage section may, at least in parts, overlap or even coincide in the axial direction. In terms of manufacturing technology and for the purpose of effective aeration of the wound, it has proven to be expedient if at least one aeration perforation penetrates an aerating lumen, preferably in the radial direction, and opens out into a drainage lumen.

In the interest of effective wound monitoring, it has proven to be expedient if the drainage tube is equipped with an X-ray contrast strip extending in the longitudinal direction of the tube. In a particularly preferred embodiment of the invention, in this arrangement, this X-ray contrast strip may extend in the axial direction in a jacket area without any aeration lumen, preferably in the jacket area of the drainage tube, which is arranged between the aeration lumens that are particularly far apart from each other in the circumferential direction. As a result, the X-ray contrast strip simultaneously forms a marking for the location, at which the perforation of the tube jacket can be implemented in a particularly easy manner without any damage to any aeration lumen.

In all the embodiments of the invention, the drainage tube is preferably made of silicone having a Shore hardness of preferably approx. 50 A. In this case, the tube can receive a so-called "LowTack" surface treatment to reduce the surface roughness. An additional coating (e.g., Parylene) for reducing the surface roughness/tack/gas permeability is also possible, but only required in a few cases. According to all the embodiments of the invention, the drainage tube may have an outside diameter of 6 mm to 10 mm, preferably approx. 8 mm. In all the embodiments of the invention, the cross-section of the exudate lumen is approximately 3 mm to 4 mm, preferably approximately 3.9 mm, The aeration lumens may have a diameter of approx. 0.5 mm to 1.5 mm, preferably approx. 1 mm. The perforations opening out into the exudate lumen, may, just like the aeration perforations, have a diameter of 2 mm to 4 mm, preferably approx. 2.8 mm.

In all the embodiments of the invention, the X-ray contrast strip may contain barium sulfate (approx. 40%). The silicone to be used within the scope of the invention is preferably gas-tight. For this purpose, care is taken to assure that the system does not lose more than 5 mm Hg at 200 Hg initial pressure within 7.5 minutes.

The special utility of a drainage tube according to the invention was explained above related to deep drainage. But a drainage tube according to the invention can also be successfully used in planar drainage. It can then be expedient for the drainage tube in the area of the surface of the wound to be treated or the wound covering to extend, at least in sections, in arcuate form. It may be designed annular, helical and/or spirally.

In this respect, it has proven to be particularly expedient if, at least in sections, the drainage tube is made of a material having a Shore hardness in the range between 40 A and 60 A. It may, for instance, be made of silicone. If the Shore hardness is less than 40 A, the tube will be so soft that it tends to kink, thus blocking the exudate lumen and/or one or a plurality of aeration lumens. When using tubes having a Shore hardness of more than 60 A, the placement of the tube extending in arcuate form is problematic because, in that case, the restoring forces counteracting the tube bend may cause detachment of the tube from the wound or the wound packing material.

Figure 2:
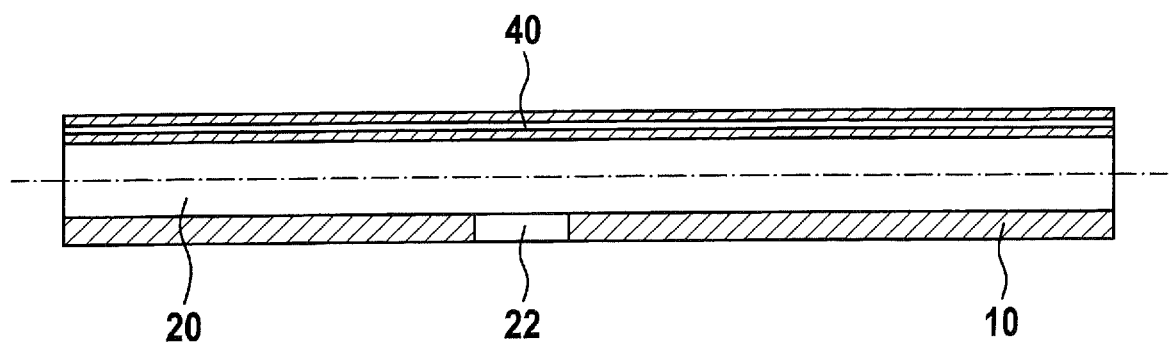
Figure 3:
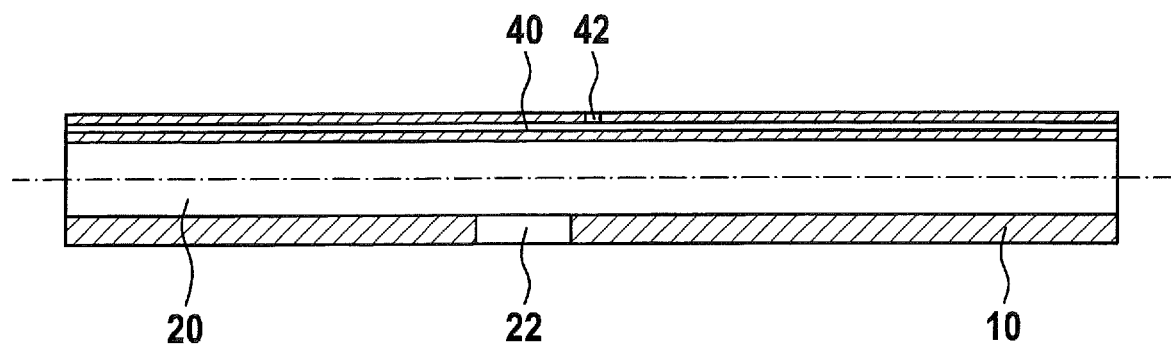
Figure 4:
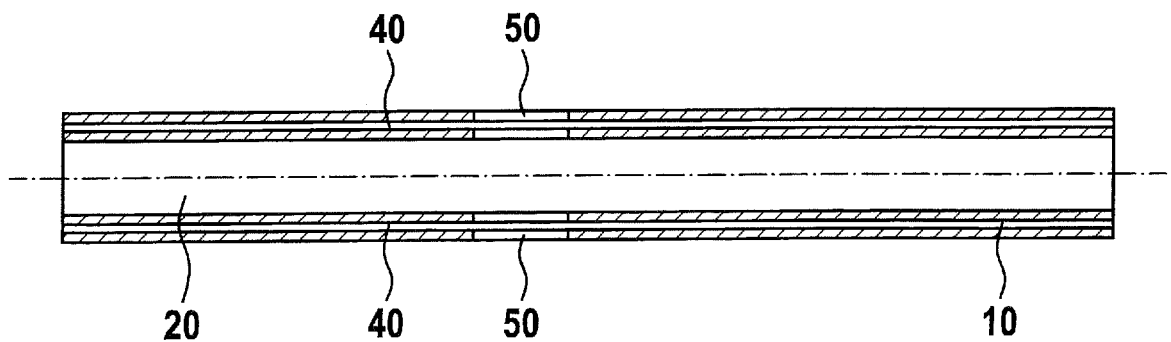
Figure 5:
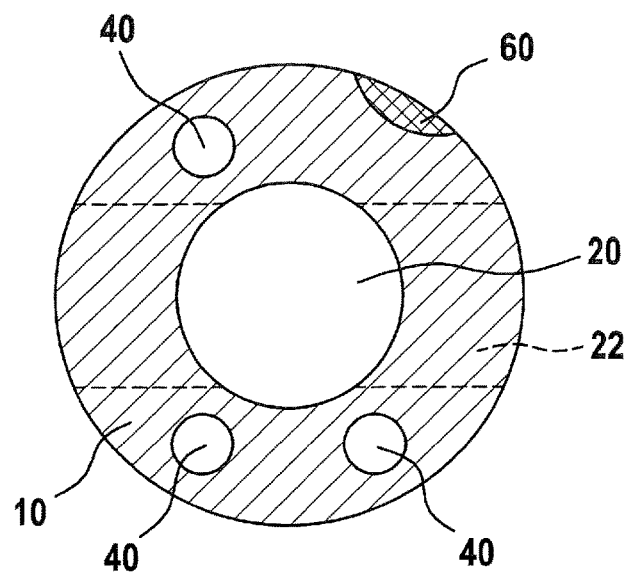
Figure 6:
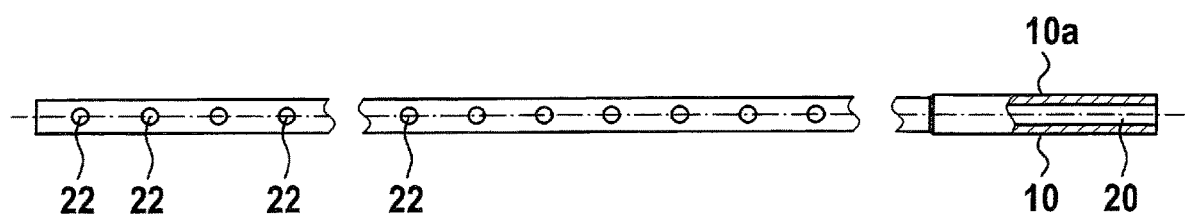

Hereinafter, the invention will be explained with reference to the drawing, to which express reference is made with respect to all characteristics, which are essential to the invention and which are not expressly exposed in detail in the specification. The drawing shows the following:

FIG. 1, a perspective view of a drainage tube according to the invention in accordance with a first embodiment of the invention, FIG. 2, an axial section view of the drainage tube according to FIG. 1, FIG. 3, an axial section view of a drainage tube according to a second embodiment of the invention, FIG. 4, an axial section view of a drainage tube according to a third embodiment of the invention, FIG. 5, a radial section view of a drainage tube according to a fourth embodiment of the invention, and FIG. 6, a view of a drainage tube according to the invention.

The drainage tube illustrated in FIG. 1 comprises a tube jacket 10 having an outer circular cylinder jacket-shaped boundary area, which encircles an exudate lumen 20.

Exudate lumen 20 is designed coaxial with the tube axis. In this design, the tube has a total diameter of 8 mm, the exudate lumen having a diameter of approximately 4 mm. Tube jacket 10 is axially penetrated by a total of three aeration lumens 40, which are arranged radially offset with reference to the drainage lumen on a circular line encircling the tube axis. The aeration lumens 40 are arranged uniformly offset with reference to each other in the circumferential direction. Tube jacket 10 is penetrated by a number of perforations 22, which are arranged one behind the other in the axial direction and each of which, starting at the outer boundary area of tube jacket 10, opens out into drainage lumen 20. The perforations 22 are also designed approximately in circular cylinder jacket-shape and have a diameter of approximately 2.8 mm.

In the embodiment of the invention illustrated in FIG. 1, the centers of the perforations 22 are arranged on straight lines running parallel to the tube axis. In the embodiment of the invention shown in FIG. 1, the aeration lumens 40 open out in front, while the effective suction surface is enlarged by providing the perforations 22 in such a way that, in addition to a frontal suction surface, suction surfaces are additionally provided in the area of the outer boundary area of the tube jacket. This arrangement is also shown schematically in the axial section view according to FIG. 2.

The embodiment according to FIG. 3 essentially differs from the embodiment of the invention illustrated based on FIGS. 1 and 2 in that aeration lumen 40 has not only a frontal opening but is also connected to the environment via an aeration perforation 42. The aeration perforation penetrates the outer boundary area of tube jacket 10 and opens out into aeration lumen 40 without reaching exudate lumen 20, which, in turn, is connected to the environment via perforation 22.

In the embodiment of the invention illustrated in FIG. 4, instead of the perforations 22 and 42, perforations 50 are provided which, starting at the outer boundary area of tube jacket 10 and extending in a radial direction, initially penetrate the aeration lumens 40 and thereupon open out into exudate lumen 20. The perforations 50 extend in a radial direction and can be produced by a drilling or punching operation on the drainage tube. Appropriate drainage tubes are comparatively easy to manufacture.

In the embodiment of the invention illustrated in FIG. 5, in addition to an exudate lumen 20 extending coaxial with the tube axis, a total of three aeration lumens 40 are provided, each of which has a smaller cross-section or smaller diameter than exudate lumen 20. The aeration lumens 40 are arranged radially offset at equal intervals with reference to the tube axis or the axis of the drainage lumen and, in the radial intersecting plane shown in FIG. 5, are situated on the vertices of a right triangle. In this arrangement, the tube jacket extends between two exudate lumens in the circumferential direction over an angle of approx. 180°, while between the other aeration lumens, it extends over peripheral angles of 60° and 120°, respectively. In this manner, a particularly large amount of space is created for the creation of a perforation, which fully penetrates the drainage tube and the drainage lumen in a radial direction, without posing a risk of damage to one of the aeration lumens 40, as indicated at 22 in FIG. 5.

The perforation penetrates the area of the tube jacket, which extends over a circumferential angle of 120° between two aeration lumens, as well as the area of the tube jacket, which extends between two aeration lumens over an of angle of 180°. In the embodiment illustrated in FIG. 5, the area of the tube jacket, which extends in the circumferential direction between two aeration lumens over an angle of 180°, is marked by means of an X-ray contrast strip 60.

Hence, the X-ray contrast strip is not only used for monitoring wound care per se but also for producing a drainage tube according to the invention by perforating of an intermediate product, while avoiding damage to the aeration lumens.

As shown in FIG. 6, in the axial direction of the drainage tube, the perforations are arranged at invariable distances. In this manner, homogeneous aspiration of wound fluids or exudates can take place. If it is necessary to treat wounds in which wound fluid forms centrally in some locations, the distances between the perforations may vary accordingly. As indicated at 10a in FIG. 6, at least in sections, drainage tube 10 may have a sheath to a for improving the draw-off forces. Sheath 10a for tube 10 may be provided in the non-perforated area of the drainage tube. It may consist entirely or partially of PVC.

A treatment kit equipped with a drainage tube according to the invention has moreover, in addition to the drainage tube, a wound packing material and an occlusive film for producing a wound space containing the wound and a wound packing material, the drainage tube being insertable into the wound space. For this purpose, it may penetrate the occlusive film or be inserted into the drainage space between the skin and the occlusive film. Expediently, the treatment kit will be additionally equipped with a pump which can, on the one hand, generate a negative pressure in the wound space via the drainage lumen of the drainage tube connected thereto, and, on the other hand, is designed for aerating the wound space via at least one aeration lumen of the drainage tube connected thereto. The invention is not limited to the embodiments described with reference to the drawing. Rather, the provision of drainage tubes according to the invention having less than three and more than three aeration lumens is also intended. The perforations may be provided at irregular intervals in the axial direction. The perforations may penetrate both an aeration lumen and the drainage lumen. The openings provided in the drainage tube, both the frontal openings of the drainage lumens and the peripheral perforation openings, may be covered by something like a window screen mesh or mesh grid to prevent wound packing material or the like from being sucked into the tube. Aeration should reach all the way to the end of the drain via one or a plurality of continuous channels. At the pump end of the drainage tube, a sheath of a high-strength material, such as polyvinyl chloride, may be attached on the outside of the tube, in order to assure an increased draw-off force of the connection to the pump.

The invention claimed is:

1. A drainage tube for use in wound drainage, comprising:
a drainage lumen surrounded by a tube jacket and extending parallel to a tube axis;
wherein the tube jacket has at least one drainage perforation which, starting at an outer boundary area of the tube jacket, extends in a transverse direction to the tube axis and opens out into the drainage lumen;
wherein the tube jacket is penetrated by at least one aeration lumen which extends parallel to the tube axis and is separated, at least in sections, from the drainage lumen by at least a portion of a tube jacket area situated radially inside of the aeration lumen;
wherein two or more of the aeration lumens are offset against each other in a circumferential direction of the tube jacket and penetrate the tube jacket; and
wherein the offset between two of the aeration lumens adjacent one another in the circumferential direction of the drainage tube is greater than 360°/n, where n denotes the number of the aeration lumens.

2. The drainage tube of claim 1, wherein the drainage perforation, starting an outer boundary area of the tube jacket, extends perpendicular to the tube axis.

3. The drainage tube of claim 1, wherein the tube jacket has at least one drainage section having two or more of the drainage perforations opening out into the drainage lumen and a line section without any drainage perforations, wherein an axial length of the line section without any drainage perforations is longer than an axial distance between the most distantly located drainage perforations in the drainage section.

4. The drainage tube of claim 1, wherein the offset between two of the aeration lumens adjacent one another in the circumferential direction of the drainage tube is in the range from 120° to 240°.

5. The drainage tube of claim 4, wherein the offset between two of the aeration lumens adjacent one another in the circumferential direction of the drainage tube is in the range from 150° to 210°.

6. The drainage tube of claim 5, wherein the offset between two of the aeration lumens adjacent one another in the circumferential direction of the drainage tube is in the range from 170° to 190°.

7. The drainage tube of claim 1, wherein the drainage tube comprises three aeration lumens.

8. The drainage tube of claim 7, wherein longitudinal axes of two of the aeration lumens are situated approximately parallel to a longitudinal axis of the drainage lumen, and are 180° apart from each other relative to the longitudinal axis of the drainage lumen.

9. The drainage tube of claim 7, wherein longitudinal axes of the aeration lumens in a radial intersecting plane form vertices of a right triangle.

10. The drainage tube of claim 1, wherein longitudinal axes of the aeration lumens have approximately equal radial distances from a longitudinal axis of the drainage lumen.

11. The drainage tube of claim 1, wherein at least one of the aeration lumens in a radial intersecting plane has a smaller cross-sectional area than the drainage lumen.

12. The drainage tube of claim 11, wherein all aeration lumens in a radial intersecting plane have a smaller cross-sectional area than the drainage lumen.

13. The drainage tube of claim 1, wherein the tube jacket has at least one aeration perforation which, starting at an outer boundary area of the tube jacket, extends in a transverse direction to the tube axis, and opens out into the at least one aeration lumen.

14. The drainage tube of claim 13, wherein the aeration perforation, starting at an outer boundary of the tube jacket, extends approximately perpendicular to the tube axis.

15. The drainage tube of claim 13, wherein the tube jacket has at least one aeration section having two or more of the aeration perforations opening out into at least one of the aeration lumens and a line section without any aeration perforations, wherein an axial length of the line section without any aeration perforation is longer than an axial distance between the most distantly located aeration perforations in the aeration section.

16. The drainage tube of claim 15, wherein the tube jacket has at least one drainage section having two or more of the drainage perforations opening out into the drainage lumen; and wherein the aeration section and the drainage section overlap at least partially in an axial direction.

17. The drainage tube of claim 13, wherein the aeration perforation penetrates the aeration lumen and opens out into the drainage lumen.

18. The drainage tube of claim 17, wherein the aeration perforation penetrates the aeration lumen in a radial direction.

19. The drainage tube of claim 1, further comprising an X-ray contrast strip extending in a longitudinal direction of the drainage tube.

20. The drainage tube of claim 19, wherein the X-ray contrast strip extends in a jacket surface area without any aeration lumen.

21. The drainage tube of claim 1, wherein, at least in sections, the drainage tube is made of a material having a Shore hardness in the range from 40 A to 60 A.

22. The drainage tube of claim 21, wherein the material is silicone.

23. A treatment kit comprising:
a wound packing material;
an occlusive film configured to cover a wound space containing a wound and the packing material; and
the drainage tube of claim 1 configured for insertion into the wound space.

24. The treatment kit of claim 23, further comprising a pump configured to generate a negative pressure in the wound space via the drainage lumen of the drainage tube connected to it and/or the wound space can be aerated via at least one aeration lumen of the drainage tube connected to it.

* * * * *